United States Patent [19]
Holton et al.

[11] Patent Number: 5,948,955
[45] Date of Patent: *Sep. 7, 1999

[54] TRANSGENIC PLANTS HAVING ALTERED ANTHOCYANN LEVELS

[75] Inventors: Timothy Albert Holton, Northcote; Yoshikazu Tanaka, Rosanna, both of Australia

[73] Assignee: International Flower Developments Pty Ltd, Victoria, Australia

[ * ] Notice: This patent is subject to a terminal disclaimer.

[21] Appl. No.: 08/553,315

[22] PCT Filed: May 20, 1994

[86] PCT No.: PCT/AU94/00265

§ 371 Date: Jan. 24, 1996

§ 102(e) Date: Jan. 24, 1996

[87] PCT Pub. No.: WO94/28140

PCT Pub. Date: Dec. 8, 1994

Related U.S. Application Data

[63] Continuation-in-part of application No. 08/285,309, Aug. 3, 1994, Pat. No. 5,569,832, which is a continuation of application No. 07/912,900, Jul. 13, 1991, Pat. No. 5,349,125.

[30] Foreign Application Priority Data

May 20, 1993 [AU] Australia .............................. PL 8862/93
Mar. 24, 1994 [AU] Australia .......................... PM 4698/94

[51] Int. Cl.⁶ ............................... A01H 5/00; C12N 5/14; C12N 15/29; C12N 15/52; C12N 15/82
[52] U.S. Cl. ...................... 800/298; 435/320.1; 435/419; 435/468; 536/23.2; 536/23.6; 800/282; 800/323; 800/323.2; 800/323.3
[58] Field of Search ........................... 800/205, DIG. 10, 800/12, 36, 67, 68; 435/172.3, 320.1, 419, DIG. 12, DIG. 36; 536/23.2, 23.6

[56] References Cited

U.S. PATENT DOCUMENTS 5,569,832 10/1996 Holton et al. ........................... 800/205

FOREIGN PATENT DOCUMENTS

B-19530/92 1/1993 Australia .

OTHER PUBLICATIONS

Kaulen et al. (1986) The EMBO Journal vol. 5 (1): pp. 1–8.

The American Heritage Dictionary, 2nd college edition, Houghton Miflin Co., Boston, 1982, p. 660.

Ohbayashi et al. (1993) "Molecular Cloning of cDNA Encoding Flavonoid–3', 5'–Hydroxylase from *Petunia Hybrida* I: Identification of blue flower specific cDNA fragment encoding cytochrome P450" *Plant Cell Physiol.* 34:s16 (Abstract 028(1pB05)).

Shimada et al. (1993) "Molecular Cloning of cDNA Encoding Flavonoid–3', 5'–Hydroxylase from *Petunia Hybrida* II: Cloning of the full length cDNA and its expression in transgenic plants" *Plant Cell Physiol. 34*:s17 (Abstract 029(1pB06)).

Holten et al. (1993) "Cloning and Expression of Cytochrome P450 Genes Controlling Flower Colour" *Nature* 366:276–279.

Toguri et al. (1993) "Activation of Anthocyanin Synthesis Genes by White Light in Eggplant Hypocotyl Tissues, and Identification of an Inducible P–450 cDNA" *Plant Mol. Biol.* 23:933–946.

Toguri et al. (1993) "The Cloning and Characterization of a cDNA Encoding a Cytochrome P450 from the Flowers of *Petunia hybrida*" *Plant Sci.* 94:119–126.

Primary Examiner—Douglas W. Robinson
Assistant Examiner—Amy J. Nelson
Attorney, Agent, or Firm—Scully & Scott, Murphy & Presser

[57] ABSTRACT

The present invention relates generally to transgenic flowering plants. More particularly, the present invention is directed to transgenic rose, carnation and chrysanthemum plants genetically modified to enable expression of flavonoid 3',5'-hydroxylase thereby permitting the manipulation of intermediates in the flavonoid pathway.

38 Claims, 11 Drawing Sheets

5,948,955

TRANSGENIC PLANTS HAVING ALTERED ANTHOCYANN LEVELS

CROSS REFERENCE TO RELATED APPLICATIONS

The present application is a continuation-in-part of U.S. patent application Ser. No. 08/285,309, filed Aug. 3, 1994, now U.S. Pat. No. 5,569,832, which, in turn, is a continuation of Ser. No. 07/912,900, filed Jul. 13, 1991, now U.S. Pat. No. 5,349,125.

The present invention relates generally to transgenic flowering plants. More particularly, the present invention is directed to transgenic rose, carnation and chrysanthemum plants genetically modified to enable expression of flavonoid 3',5'-hydroxylase thereby permitting the manipulation of intermediates in the flavonoid pathway.

BACKGROUND OF THE INVENTION

The flower industry strives to develop new and different varieties of flowering plants with improved characteristics ranging from disease and pathogen resistance to altered inflorence. Although classical breeding techniques have been used with some success this approach has been limited by the constraints of a particular species' gene pool. It is rare, for example, for a single species to have a full spectrum of coloured varieties. Accordingly, substantial effort has been directed towards attempting to generate transgenic plants exhibiting the desired characteristics. The development of blue varieties of the major cutflower species rose, carnation and chrysanthemum, for example, would offer a significant opportunity in both the cutflower and ornamental markets.

Flower colour is predominantly due to two types of pigment: flavonoids and carotenoids. Flavonoids contribute to a range of colours from yellow to red to blue. Carotenoids impart an orange or yellow tinge and are commonly the only pigment in yellow or orange flowers. The flavonoid molecules which make the major contribution to flower colour are the anthocyanins which are glycosylated derivatives of cyanidin, delphinidin, petunidin, peonidin, malvidin and pelargonidin, and are localised in the vacuole. The different anthocyanins can produce marked differences in colour. Flower colour is also influenced by co-pigmentation with colourless flavonoids, metal complexation, glycosylation, acylation, methylation and vacuolar pH (Forkmann, 1991).

The biosynthetic pathway for the flavonoid pigments (hereinafter referred to as the "flavonoid pathway") is well established and is shown in FIG. 1 (Ebel and Hahlbrock, 1988; Hahlbrock and Grisebach, 1979; Wiering and de Vlaming, 1984; Schram et al., 1984; Stafford, 1990). The first committed step in the pathway involves the condensation of three molecules of malonyl-CoA with one molecule of p-coumaroyl-CoA. This reaction is catalysed by the enzyme chalcone synthase (CHS). The product of this reaction, 2',4,4',6'-tetrahydroxychalcone, is normally rapidly isomerized to produce naringenin by the enzyme chalcone flavanone isomerase (CHI). Naringenin is subsequently hydroxylated at the 3 position of the central ring by flavanone 3-hydroxylase (F3H) to produce dihydrokaempferol (DHK).

The B-ring of dihydrokaempferol can be hydroxylated at either the 3', or both the 3' and 5' positions, to produce dihydroquercetin (DHQ) and dihydromyricetin (DHM), respectively. Two key enzymes involved in this pathway are flavonoid 3'-hydroxylase and flavonoid 3',5'-hydroxylase. The flavonoid 3'-hydroxylase acts on DHK to produce DHQ and on naringenin to produce eriodictyol. The flavonoid 3',5'-hydroxylase (hereinafter referred to as 3',5'-hydroxylase) is a broad spectrum enzyme catalyzing hydroxylation of naringenin and DHK in the 3' and 5' positions and of eriodictyol and DHQ in the 5' position (Stotz and Forkmann, 1982), in both instances producing pentahydroxyflavanone and DHM, respectively. The pattern of hydroxylation of the B-ring of anthocyanins plays a key role in determining petal colour.

Because of the aforesaid gene pool constraints, many of the major cutflower species lack the 3',5'-hydroxylase and consequently cannot display the range of colours that would otherwise be possible. This is particularly the case for roses, carnations and chrysanthemums, which constitute a major proportion of the world-wide cutflower market. There is a need, therefore, to modify plants and in particular roses, carnations and chrysanthemums, to generate transgenic plants which are capable of producing the 3',5'-hydroxylase thereby providing a means of modulating DHK metabolism, as well as the metabolism of other substrates such as DHQ, naringenin and eriodictyol. Such modulation influences the hydroxylation pattern of the anthocyanins and allows the production of anthocyanins derived from delphinidin, thereby modifying petal colour and allowing a single species to express a broader spectrum of flower colours. There is a particular need to generate transgenic plants which produce high levels of anthocyanins derived from delphinidin. In accordance with the present invention, gene constructs are generated and used to make transgenic plants which express high levels of delphinidin and/or its derivatives relative to non-transgenic plants of the same species. It has been determined in accordance with the present invention that genetic constructs which comprise a promoter from a gene encoding a flavonoid pathway enzyme operably linked to a flavonoid 3',5'-hydroxylase are capable of directing expression of high levels of delphinin-derived anthocyanins. The production of these high levels of delphinidin and related molecules is particularly useful in developing a range of plants exhibiting altered flower color properties.

SUMMARY OF THE INVENTION

Accordingly, one aspect of the present invention contemplates a transgenic plant selected from rose, carnation and chrysanthemum or progeny or flowering parts thereof wherein said plant carries a genetic construct comprising a promoter from a gene encoding an enzyme of the flavonoid pathway operably linked to a gene encoding a flavonoid 3',5'-hydroxylase wherein said transgenic plant produces higher levels of anthocyanins derived from delphinidin relative to non-transgenic plants of the same species.

Preferably, the flavonoid 3',5'-hydroxylase is of petunia, verbena, delphinum, grape, iris, freesia, hydrangea, cyclamen, potato, pansy, egg plant, lisianthus or campanula origin.

Most preferably, the flavonoid 3',5'-hydroxylase is of petunia origin.

The gene construct of the present invention comprises a nucleic acid molecule encoding a sequence encoding 3',5'-hydroxylase and where necessary comprises additional genetic sequences such as promoter and terminator sequences which allow expression of the molecule in the transgenic plant. When the gene construct is DNA it may be cDNA or genomic DNA. Preferably, the DNA is in the form of a binary vector comprising a chimaeric gene construct which is capable of being integrated into a plant genome to produce the transgenic plant of the present invention. The chimaeric gene construct carries a plant promoter from a gene encoding an enzyme of the flavonoid pathway. A preferred promoter is from the gene encoding chalcone synthase (CHS) and is referred to herein as the "CHS promoter". The CHS promoter is particularly preferred since it directs the high level expression of genetic sequences operably linked down stream thereof. The most preferred binary vectors are pCGP484, pCGP485, pCGP653 and pCGP1458. pCGP484 was deposited with the Australian Government Analytical Laboratories (AGAL), 1 Suakin Street, Pymble, NSW 2073, Australia, on Aug. 14, 1998 and has been accorded Accession No. NM 98/07526. pCGP485 was deposited at the same depository on the same date and accorded Accession No. NM 98/07527. pCGP653 and pCGP1458 were also deposited with the Australian Government Analytical Laboratories on Aug. 14, 1998 and accorded Accession Nos. NM 98/07524 and NM 98/07525, respectively.

By "nucleic acid molecule" as used herein is meant any contiguous series of nucleotide bases specifying a sequence of amino acids in 3',5'-hydroxylase. The nucleic acid may encode the full length enzyme or a functional derivative thereof. By "derivative" is meant any single or multiple amino acid substitutions, deletions, and/or additions relative to the naturally-occurring enzyme. In this regard, the nucleic acid includes the naturally-occurring nucleotide sequence encoding 3',5'-hydroxylase or may contain single or multiple nucleotide substitutions, deletions and/or additions to said naturally-occurring sequence. The terms "analogues" and "derivatives" also extend to any functional chemical equivalent of the 3',5'-hydroxylase, the only requirement of the said nucleic acid molecule being that when used to produce a transgenic plant in accordance with the present invention said transgenic plant exhibits one or more of the following properties:

(i) production of 3',5'-hydroxylase-specific mRNA;
(ii) production of 3',5'-hydroxylase protein;
(iii) production of delphinidin and/or its derivatives; and/or
(iv) altered flower color.

More particularly, said transgenic plant exhibits one or more of the following properties:

(i) increased levels of 3',5'-hydroxylase-specific mRNA above non-transgenic endogenous levels;
(ii) increased production of 3',5'-hydroxylase protein;
(iii) elevated levels of production of delphinidin and/or its derivatives above non-transgenic endogenous levels; and/or
(iv) altered flower color.

The nucleic acid molecules used herein may exist alone or in combination with a vector molecule and preferably an expression-vector. Such vector molecules replicate and/or express in eukaryotic and/or prokaryotic cells. Preferably, the vector molecules or parts thereof are capable of integration into the plant genome. The nucleic acid molecule may additionally contain a sequence useful in facilitating said integration and/or a promoter sequence capable of directing expression of the nucleic acid molecule in a plant cell. The nucleic acid molecule and promoter may be introduced into the cell by any number of means such as by electroporation, micro-projectile bombardment or Agrobacterium-mediated transfer.

In accordance with the present invention, a nucleic acid molecule encoding 3',5'-hydroxylase may be introduced into and expressed in a transgenic plant selected from the list consisting of rose, carnation and chrysanthemum thereby providing a means to convert DHK and/or other suitable substrates into anthocyanin derivatives of anthocyanidins such as petunidin, malvidin and especially delphinidin. The production of these anthocyanins may contribute to the production of a variety of shades of blue colour or blue-like colour or may otherwise modify flower colour by diverting anthocyanin production away from pelargonidin, cyanidin and peonidin and their derivatives and towards delphinidin and its derivatives. Expression of the nucleic acid sequence in the plant may be constitutive, inducible or developmental. The expression "altered flower color" means any alteration in flower colour relative to the naturally-occurring flower colour taking into account normal variations between flowerings. Preferably, the altered flower color includes production of various shades of blue, purple or pink colouration different to those in the non-transgenic plant.

The present invention also contemplates a method for producing a transgenic flowering plant exhibiting elevated levels of production of delphinidin and/or its derivatives above non-transgenic endogenous levels, said method comprising introducing into a cell of a plant selected from the list consisting of rose, carnation and chrysanthemum, a nucleic acid molecule encoding a sequence encoding 3',5'-hydroxylase under conditions permitting the eventual expression of said nucleic acid molecule, regenerating a transgenic plant from the cell and growing said transgenic plant for a time and under conditions sufficient to permit the expression of the nucleic acid molecule into the 3',5'-hydroxylase enzyme. The present invention is also directed to a method for producing a transgenic plant selected from rose, carnation and chrysanthemum, said method comprising introducing into said plant a gene construct containing a nucleic acid sequence encoding a flavonoid 3',5'-hydroxylase characterised in that said transgenic plant produces higher levels of anthocyanin derived from delphinidin relative to non-transgenic plants of the same respective species.

In a preferred embodiment, the transgenic flowering plant exhibits altered flower color properties coincident with elevated levels of delphinidin production, and the altered flower color includes the production of blue flowers or other bluish shades depending on the physiological conditions of the recipient plant. In certain plant species it may be preferable to select a "high pH line", such being defined as a variety having a higher than average petal vacuolar pH. The origin of the recombinant 3',5'-hydroxylase or its mutants and derivatives may include, petunia, verbena, delphinium, grape, iris, freesia, hydrangea, cyclamen, potato, pansy, lisianthus, campanula or eggplant.

Consequently, the present invention extends to a transgenic rose, carnation or chrysanthemum plant containing all or part of a nucleic acid molecule representing 3',5'-hydroxylase and/or any homologues or related forms thereof and in particular those transgenic plants which exhibit elevated 3',5'-hydroxylase-specific mRNA and/or elevated production of delphinidin derivatives and/or altered inflorence properties. The transgenic plants, therefore, contain a stably-introduced nucleic acid molecule comprising a nucleotide sequence encoding the 3',5'-hydroxylase enzyme. The invention also extends to progeny from such transgenic plants and also to reproduction material therefor (e.g. seeds). Such seeds, especially if coloured, will be useful inter alia as proprietary tags for plants.

The present invention is further described by reference to the following non-limiting Figures and Examples.

DETAILED DESCRIPTION OF THE INVENTION

EXAMPLE 1

Materials

Figure 1:
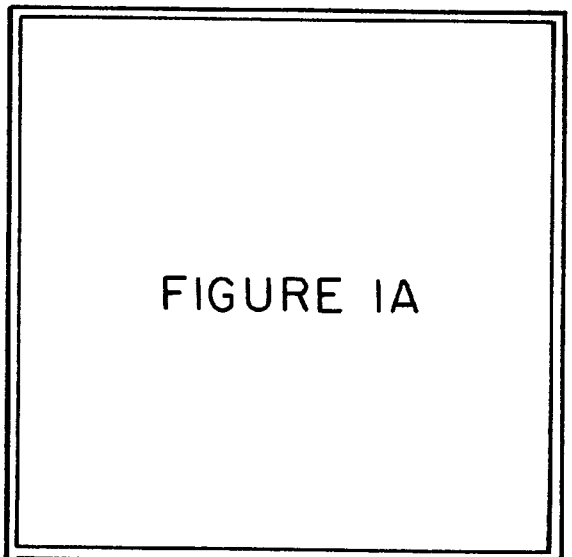
FIGS. 1A–1B are schematic representations of the biosynthesis pathway for the flavonoid pigments. Enzymes involved in the first part of the pathway have been indicated as follows: PAL=Phenylalanine ammonia-lyase; C4H=Cinnamate 4-hydroxylase; 4CL=4-coumarate: CoA ligase; CHS=Chalcone synthase; CHI=Chalcone flavanone isomerase; F3H=Flavanone 3-hydroxylase; DFR=Dihydroflavonol-4-reductase; UFGT=UDP-glucose: flavonoid-3-O-glucosyltransferase. The later steps correspond to conversions that can occur in P. hybrida flowers and include: 1=addition of a rhamnose sugar to the glucosyl residue of cyanidin-3-glucoside and delphinidin-3-glucoside; 2=acylation and 5-O-glucosylation; 3=3' methylation; 4=5' methylation; 5=3'5' methylation.
Figure 1:
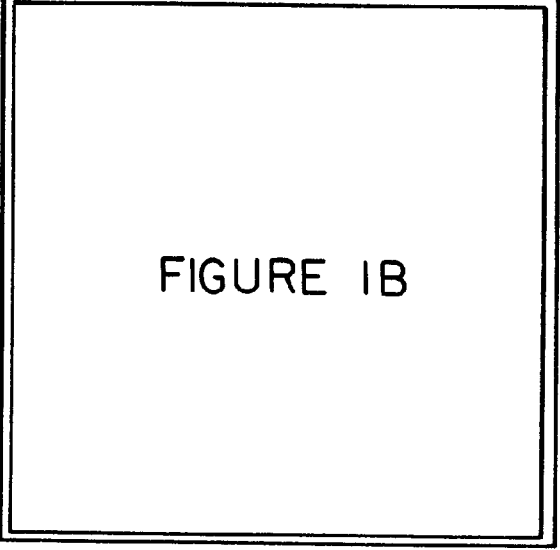
Figure 1A:
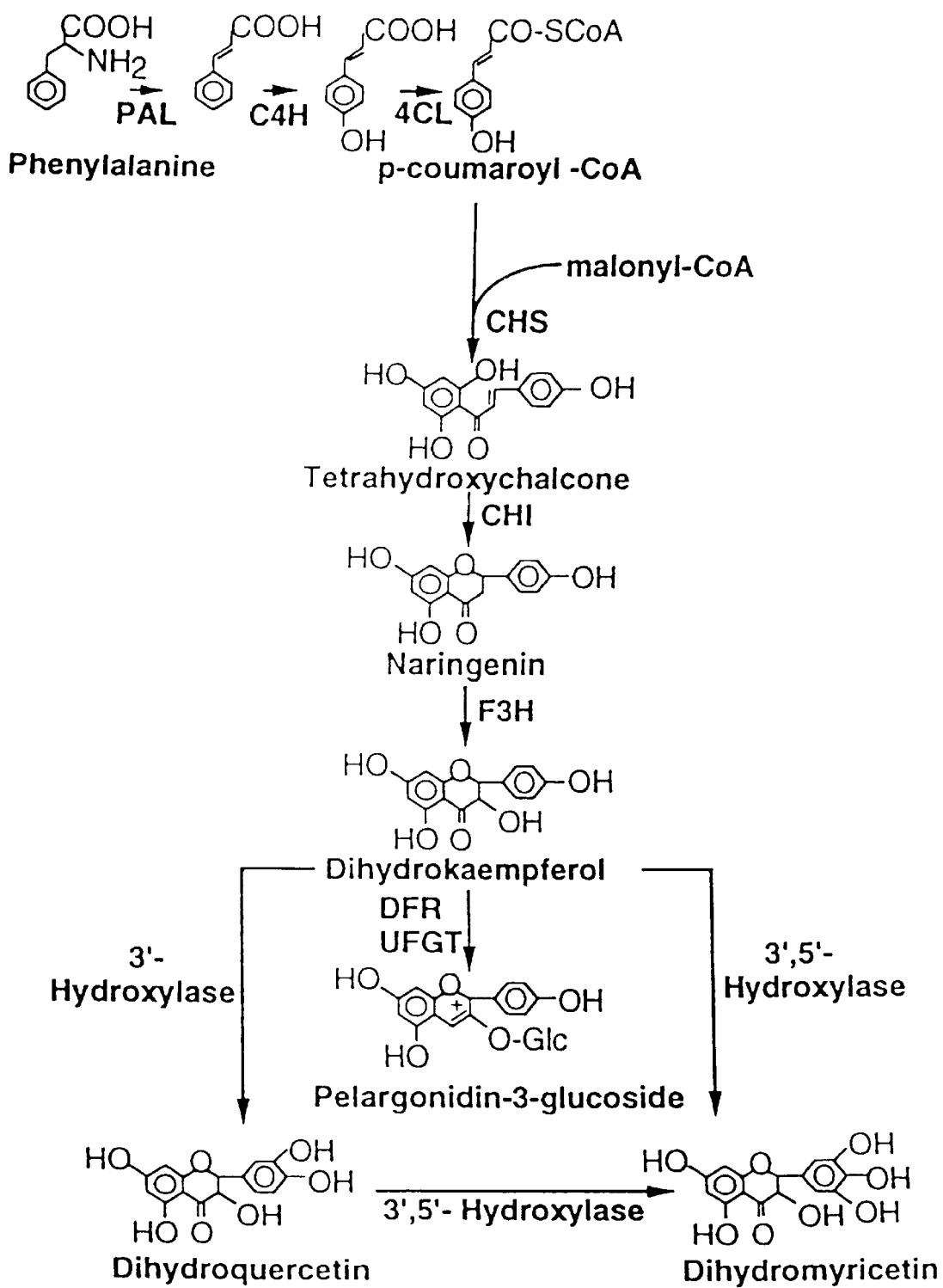
Figure 1B:
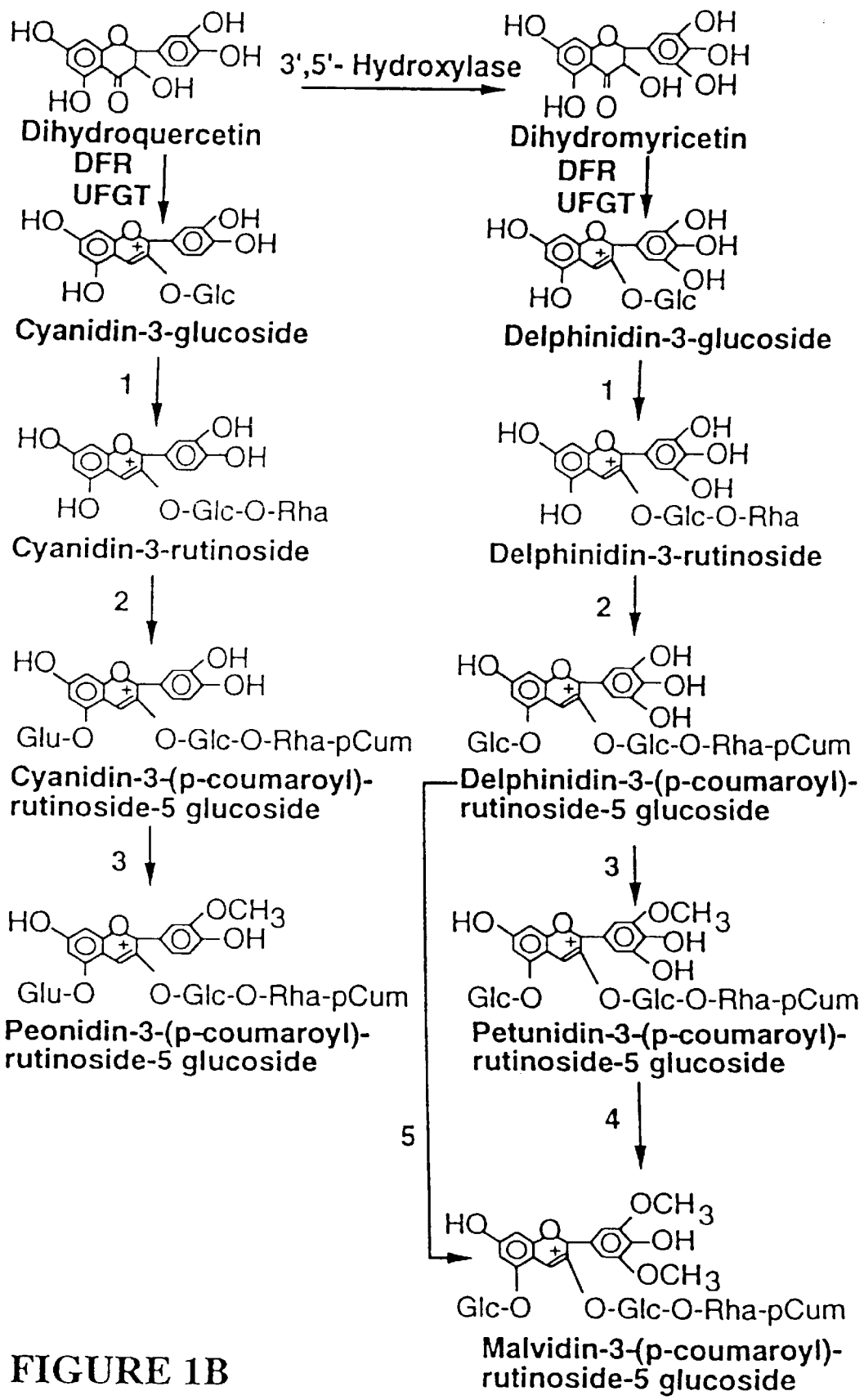

Eriodictyol and dihydroquercetin were obtained from Carl Roth KG and naringenin was obtained from Sigma. Dihydromyricetin was chemically synthesized from myricetin (Extra Synthese, France) by the method of Vercruysse et al. (1985). [$^3$H]-naringenin (5.7 Ci/mmole) and [$^3$H]-dihydroquercetin (12.4 Ci/mmole) were obtained from Amersham. All enzymes were obtained from commercial sources and used according to the manufacturer's recommendations.

The *Eschenchia coli* strain used was:

DH5α supE44, Δ(lacZYA-ArgF)U169, φ80lacZΔM15, hsdR17 ($r_k$-, $m_k$+), recA1, endA1, gyrA96, thi-1, relA1, deoR. (Hanahan, 1983 and BRL, 1986).

The disarmed *Agrobacterium tumefaciens* strains AGLO (Lazo et al., 1991) and LBA4404 (Hoekema et al., 1983) were obtained from Dr R Ludwig, Department of Biology, University of California, Santa Cruz, USA and Calgene, Inc. Calif., USA, respectively. The armed *Agrobacterium tumefaciens* strain ICMP 8317 was obtained from Dr Richard Gardner, Centre for Gene Technology, Department of Cellular and Molecular Biology, University of Auckland, New Zealand.

The cloning vector pBluescript was obtained from Stratagene.

Plants were grown in specialised growth rooms with a 14 hr day length at a light intensity of 10,000 lux minimum and a temperature of 22 to 26.

EXAMPLE 2

Construction of pCGP 90

Plasmid pCGP90 was constructed by cloning the cDNA insert from pCGP602 (International Patent Application PCT/AU92/00334; Publication Number WO 93/01290) in a sense orientation behind the Mac promoter (Comai et al., 1990) of pCGP293.

The binary expression vector pCGP293 was derived from the Ti binary vector pCGN1559 (McBride and Summerfelt, 1990). Plasmid pCGN1559 was digested with KpnI and the overhanging 3' ends were removed with T4 DNA polymerase according to standard protocols (Sambrook et al., 1989). The vector was then further digested with XbaI and the resulting 5' overhang was repaired using the Klenow fragment of DNA polymerase I. The vector was then re-ligated to give pCGP67. A 1.97 kb PstI fragment containing the Mac promoter, mas terminator and various cloning sites (Comai et al., 1990) was isolated from pCGP40 and inserted into the Pst1 site of pCGP67 to give pCGP293.

Plasmid pCGP40 was constructed by removing the GUS gene (Jefferson et al., 1987) as a BamHI-SacI fragment from pCGN7334 and replacing it with the BamHI-SacI fragment from pBluescribe M13 that includes the multicloning site. Plasmid pCGN7334 (obtained from Calgene, Inc. CA, USA), was constructed by inserting the fragment containing the chimaeric Mac-GUS-mas gene into the XhoI site of pCGN7329 (Comai et al., 1990).

The BamHI-KpnI fragment containing the above-mentioned cDNA insert was then isolated from pCGP602 and ligated with a BamHI/KpnI fragment of pCGP293. Correct insertion of the insert in pCGP90 was established by restriction analysis of DNA isolated from gentamycin resistant transformants.

EXAMPLE 3

Construction of pCGP 812

The binary expression vector pCGP812 was derived from the Ti binary vector pCGN1558 (McBride and Summerfelt, 1990). A 5.2 kb XhoI fragment containing the chimaeric mas-35S-GUS-ocs gene was isolated from pKIWI 101 Jannsen and Gardner, 1989) and sub-cloned into the XhoI site of pBluescript KS to give pCGP82. The 5.2 kb fragment was then re-isolated by HindIII/KpnI digestion and sub-cloned into the HindIII/KpnI sites of pCGN1558 to give pCGP83.

Figure 2:
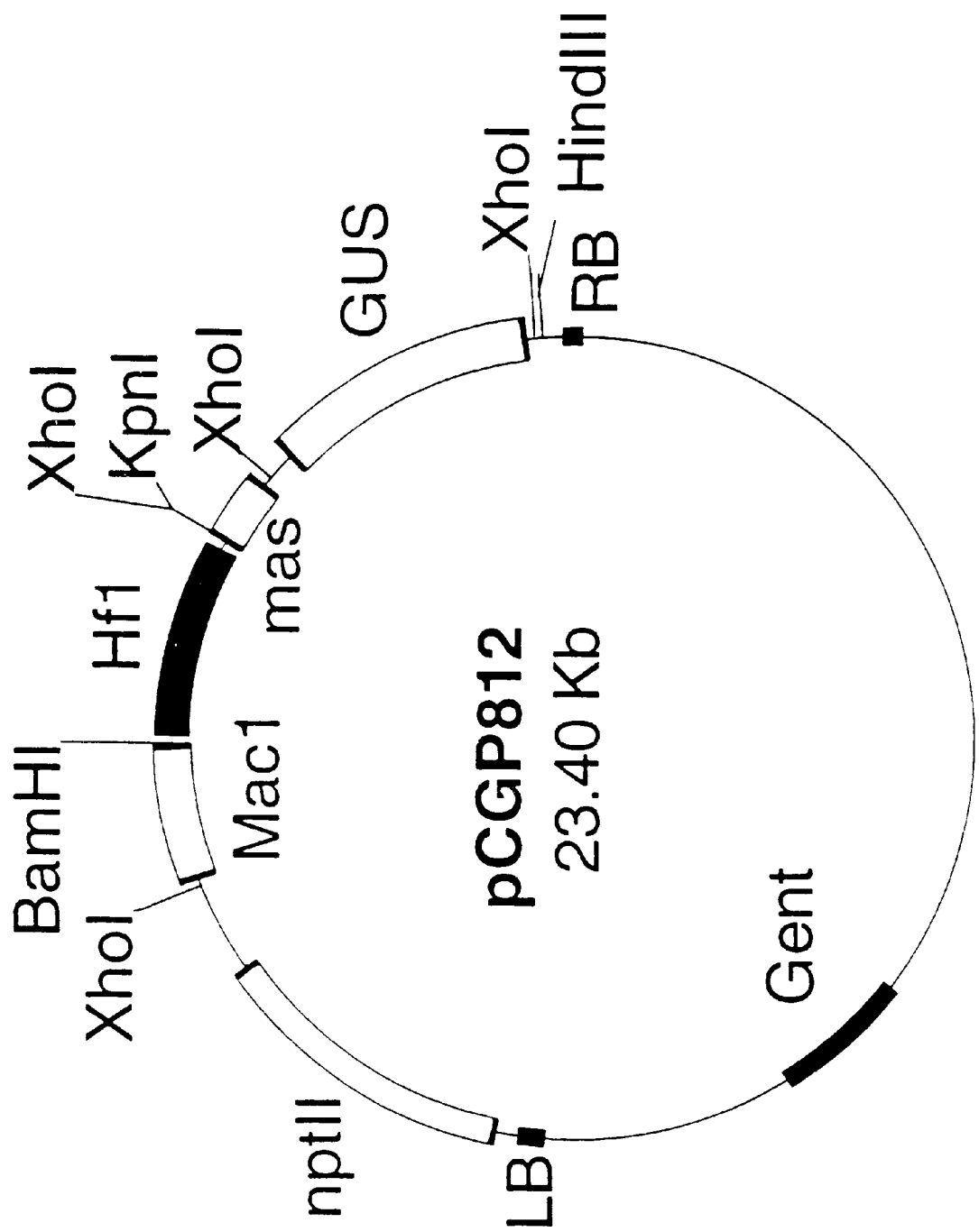
FIG. 2 is a diagrammatic representation of the binary expression vector pCGP812, contruction of which is described in Example 3. Gent=the gentamycin resistance gene; LB=left border; RB=right border; nptII=the expression cassette for neomycin phosphotransferase II; GUS=the β-glucuronidase coding region. Chimaeric gene insert is as indicated, and described in Example 3. Restriction enzyme sites are marked.
Figure 3:
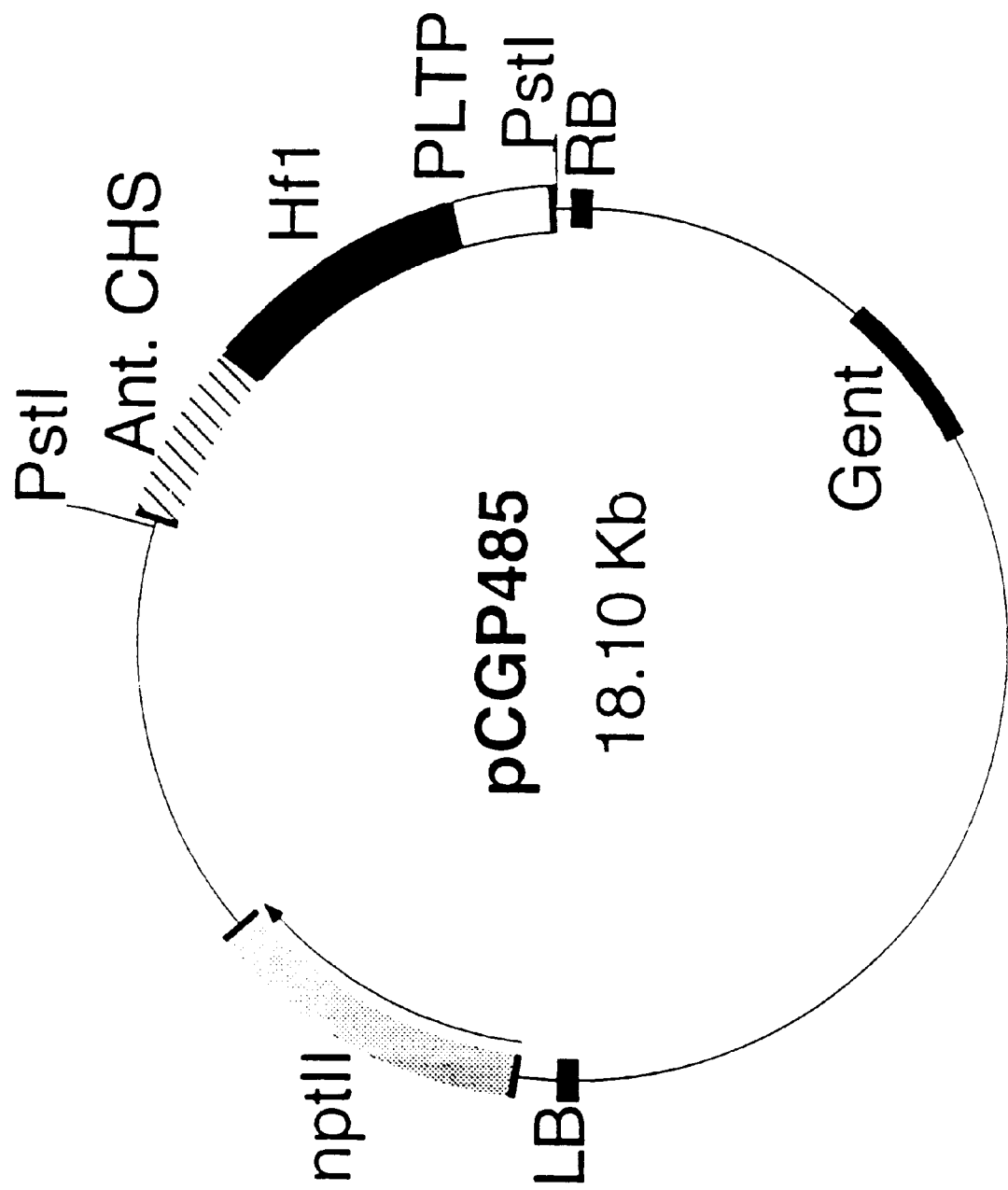
FIG. 3 is a diagrammatic representation of the binary expression vector pCGP485, contruction of which is described in Example 4. Gent=the gentamycin resistance gene; LB=left border; RB=right border; nptII=the expression cassette for neomycin phosphotransferase II. Chimaeric gene insert is as indicated, and described in Example 4. Restriction enzyme sites are marked.
Figure 4:
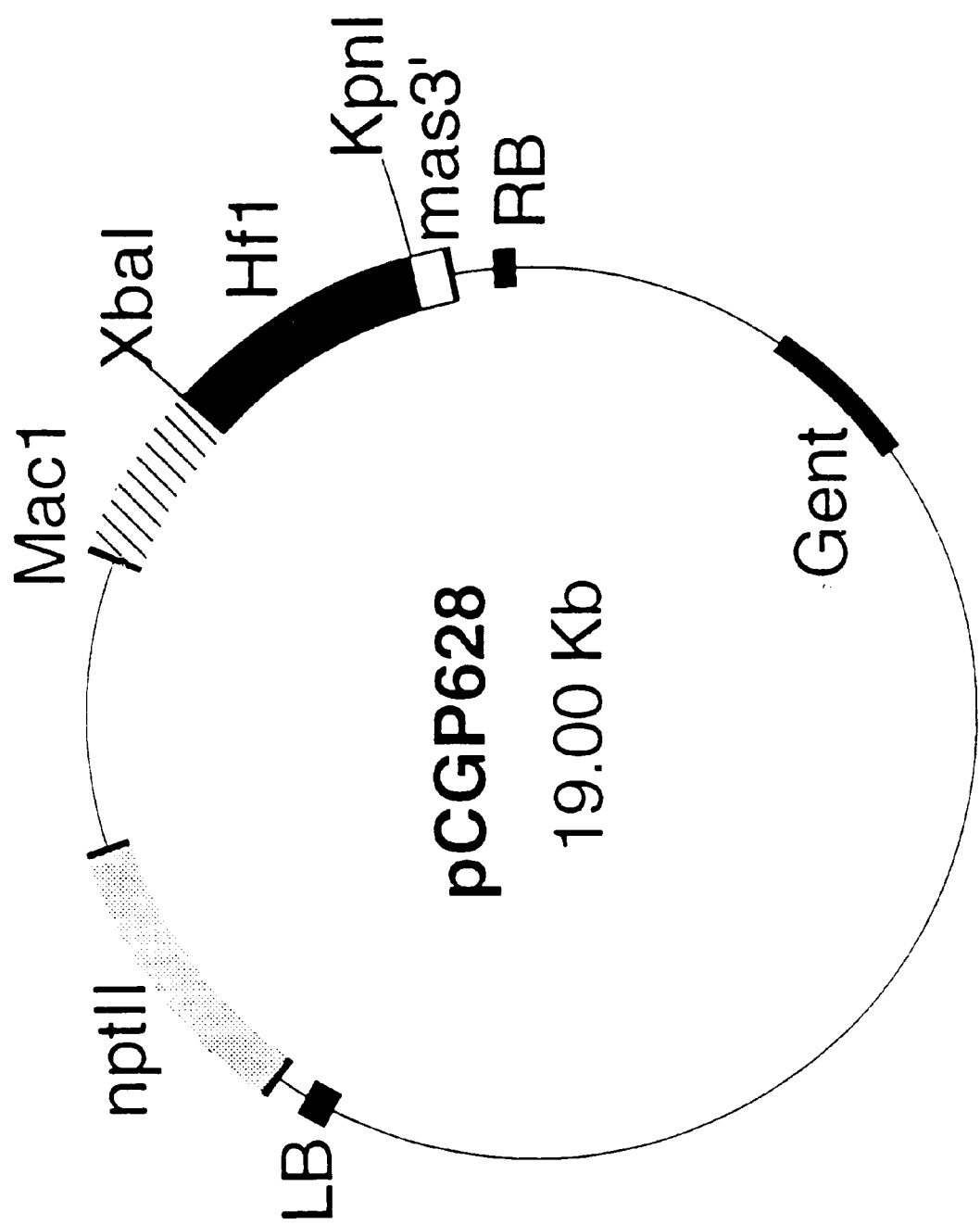
FIG. 4 is a diagrammatic representation of the binary expression vector pCGP628, contruction of which is described in Example 5. Gent=the gentamycin resistance gene; LB=left border; RB=right border; nptII=the expression cassette for neomycin phosphotransferase II. Chimaeric gene insert is as indicated, and described in Example 5. Restriction enzyme sites are marked.
Figure 5:
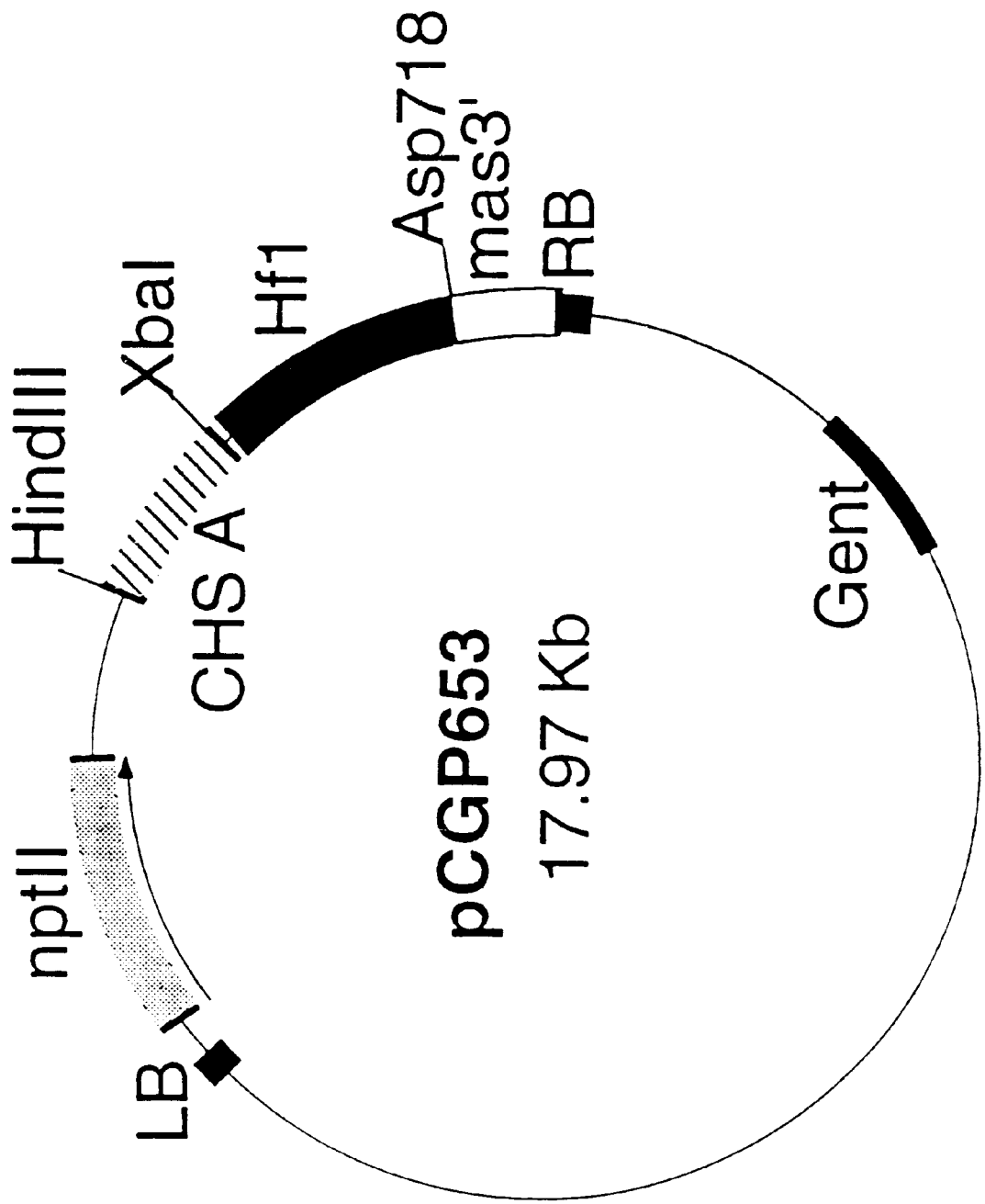
FIG. 5 is a diagrammatic representation of the binary expression vector pCGP653, contruction of which is described in Example 6. Gent=the gentamycin resistance gene; LB=left border; RB=right border; nptII=the expression cassette for neomycin phosphotransferase II. Chimaeric gene insert is as indicated, and described in Example 6. Restriction enzyme sites are marked.
Figure 6:
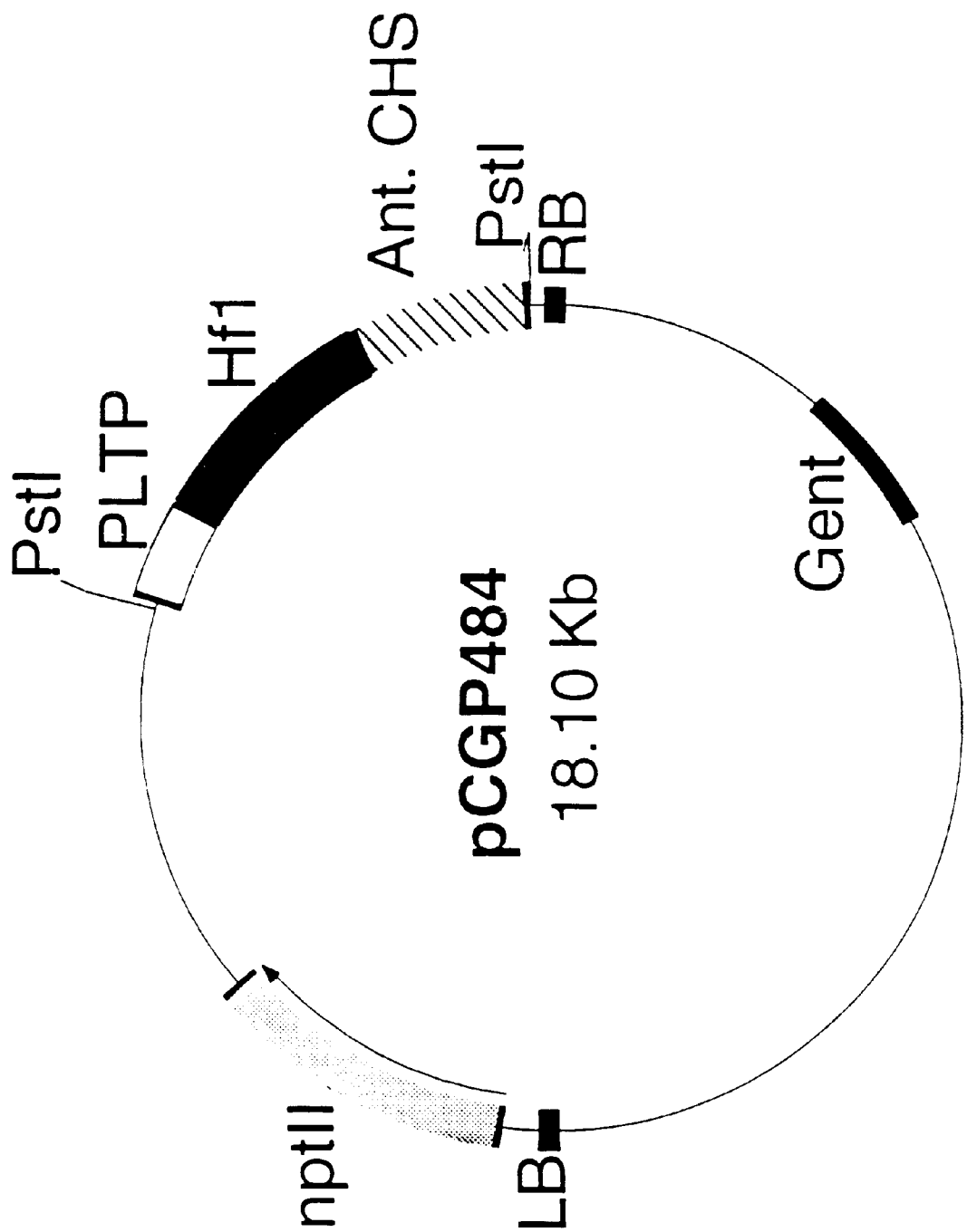
FIG. 6 is a diagrammatic representation of the binary expression vector pCGP484, contruction of which is described in Example 7. Gent=the expression cassette for the gentamycin resistance gene; LB=left border; RB=right border; nptII=neomycin phosphotransferase II. Chimaeric gene insert is as indicated, and described in Example 7. Restriction enzyme sites are marked.
Figure 7:
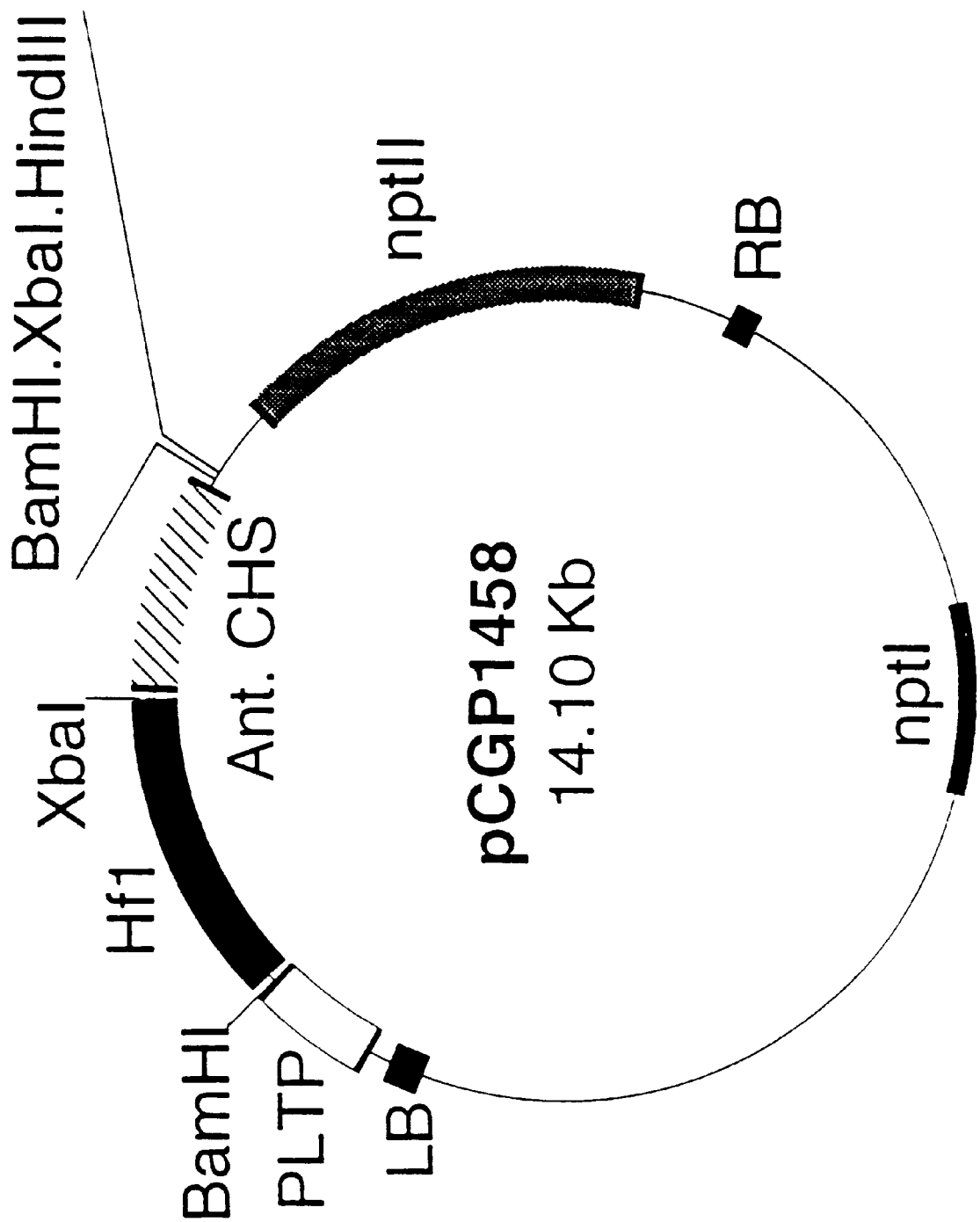
FIG. 7 is a diagrammatic representation of the binary expression vector pCGP1458, contruction of which is described in Example 8. nptI=the neomycin phosphotransferase I resistance gene; ; LB=left border; RB=right border; nptII =the expression cassette for neomycin phosphotransferase II. Chimaeric gene insert is as indicated, and described in Example 8. Restriction enzyme sites are marked.
Figure 8A:
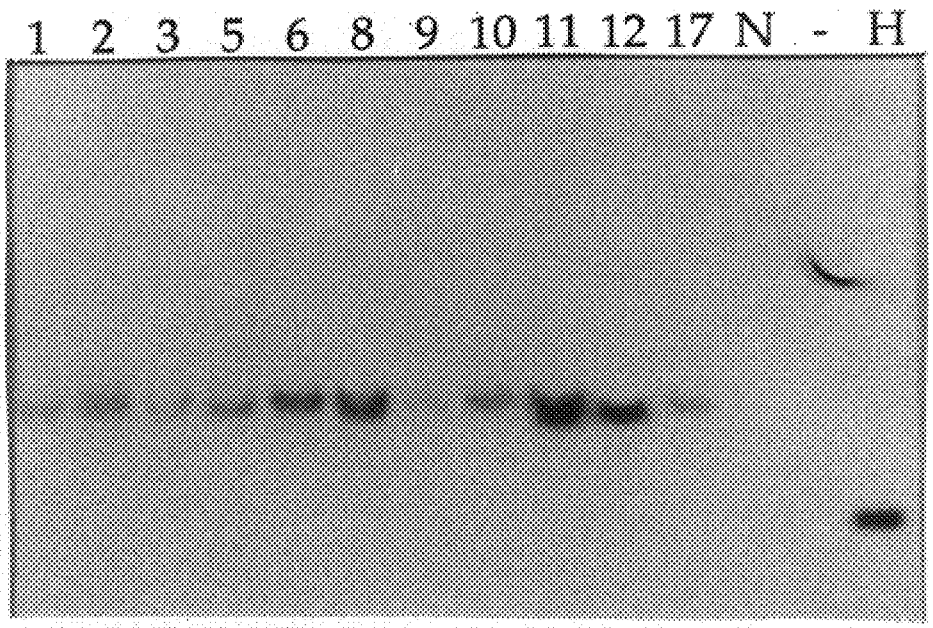
FIGS. 8A and 8B show photographs of an autoradiographic representation of a Southern hybridization of Royalty callus tissue transformed with pCGP628. Genomic DNA was digested with EcoRI and probed with the 720bp EcoRV internal fragment of Hf1 cDNA. Negative controls (N) are Royalty callus tissue transformed with pCGP 293. The positive control (H) contains 10 pg of the Hf1 fragment. The arrows indicate the 2 kb EcoRI fragment expected in transformed plants.
Figure 8B:
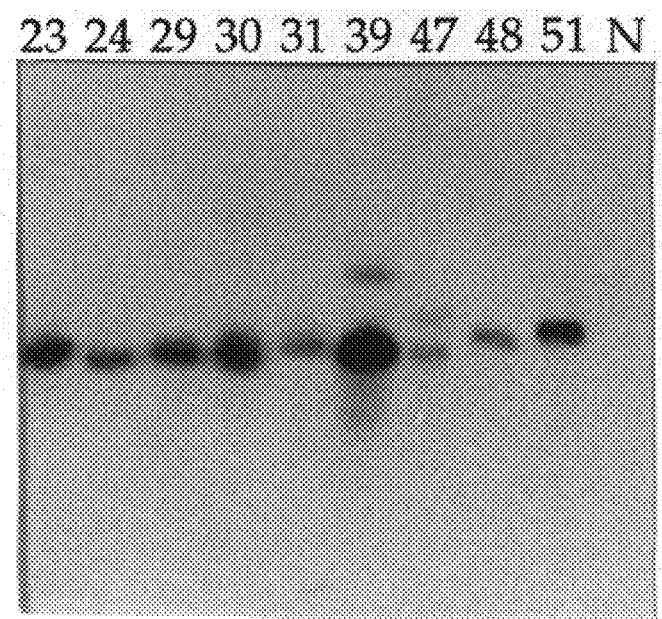
Figure 9A:
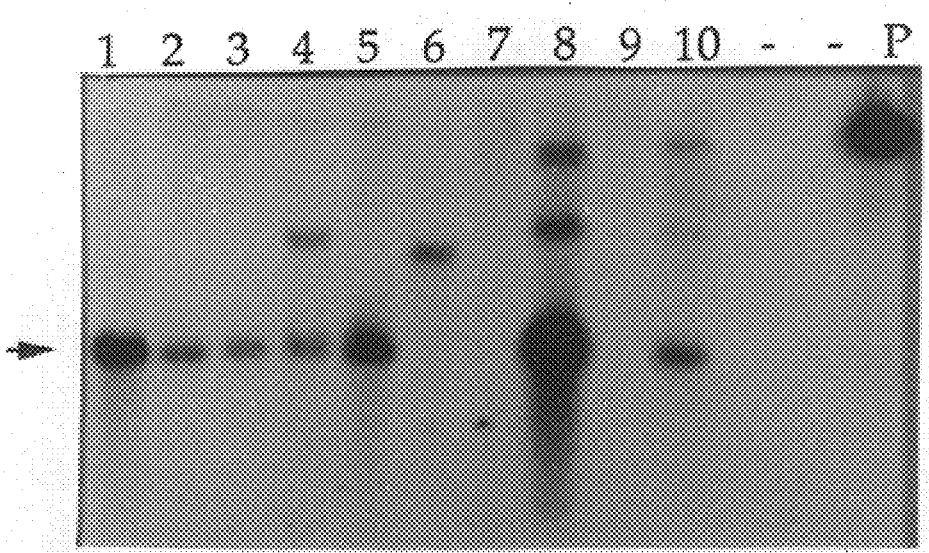
FIGS. 9A and 9B show photographs of an autoradiographic representation of a Southern hybridization of Chrysanthemum cv. Blue Ridge plants, transformed with pCGP484. Genomic DNA was digested with XbaI, which releases a 2.3 kb Hf1-PLTP fragment, and probed with a 1.8 kb FspI/BspHI fragment released from pCGP602, containing the Hf1 cDNA. Negative control (N) is genomic DNA isolated from non-transformed Blue Ridge plants. The postive control (P) is plasmid DNA of pCGP485 digested with XbaI. The arrow indicates the 2.3 kb product expected in transformed plants.
Figure 9B:
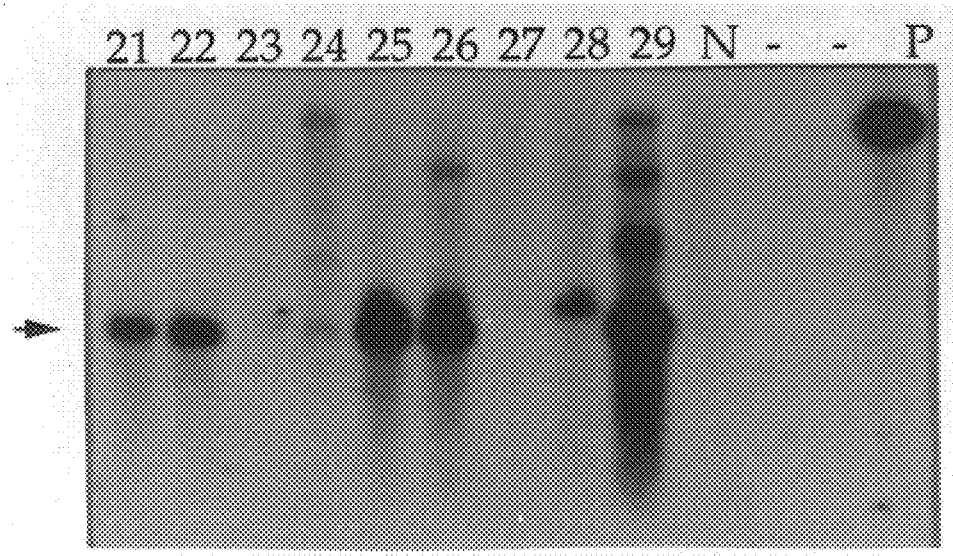

Plasmid pCGP83 was restricted with KpnI and the overhanging 3' ends were removed with T4 DNA polymerase according to standard protocols (Sambrook et al., 1989). A SmaI-BamHI adaptor (Pharmacia) was then ligated to the flushed KpnI sites to give BamHI "sticky" ends. A 3.8 kb BglII fragment containing the chimaeric Mac-Hf1-mas gene from pCGP807 (described below) was ligated with the BamHI "sticky" ends of pCGP83 to yield pCGP812 (FIG. 2).

The plasmid pCGP807 was constructed by ligating the 1.8 kb BamHI-KpnI fragment containing the above-mentioned Hf1 cDNA insert from pCGP602 with BamHI-KpnI ends of pCGP40.

EXAMPLE 4

Construction of pCGP 485

The binary vector pCGP485 was derived from the Ti binary vector pCGN1547 (McBride and Summerfelt, 1990). A chimaeric gene was constructed consisting of (i) the promoter sequence from a CHS gene of snapdragon; (ii) the coding region of the above-mentioned cDNA insert from pCGP602 from petunia, and (iii) a petunia phospholipid transferase protein (PLTP) terminator sequence. The CHS promoter consists of a 1.2 kb gene fragment 5' of the site of translation initiation (Sommer and Saedler, 1986). The petunia cDNA insert consists of a 1.6 kb BclI/FspI fragment from the cDNA clone of pCGP602 (International Patent Application PCT/AU92/00334; Publication Number WO 93/01290). The PLTP terminator sequence consists of a 0.7 kb SmaI/XhoI fragment from pCGP13Δ Bam (Holton, 1992), which includes a 150 bp untranslated region of the transcribed region of the PLTP gene. The chimaeric CHS/cDNA insert/PLTP gene was cloned into the PstI site of pCGN1547 to create pCGP485.

EXAMPLE 5

Construction of pCGP 628

Plasmid pCGP176 International Patent Application PCT/AU92/00334; Publication Number WO 93/01290) was digested with EcoRI and SpeI. The digested DNA was filled in with Klenow fragment according to standard protocols (Sambrook et al., 1989), and self-ligated. The plasmid thereby obtained was designated pCGP627. An XbaI/KpnI digest of pCGP627 yielded a 1.8 kb fragment which was ligated with a 14.5 kb fragment obtained by XbaI/KpnI digestion of pCGP293. The plasmid thus created was designated pCGP628.

EXAMPLE 6

Construction of pCGP 653

Plasmid pCGP293 (described above in Example 2) was digested with XbaI and the resulting 5' overhang was filled in using Klenow fragment according to standard protocols (Sambrook et al., 1989). It was then digested with HindIII. During this procedure, the Mac promoter (Comai et al., 1990) was deleted. A 0.8 kb petunia CHS-A promoter from pCGP669 (described below) was ligated into this backbone as a blunt-ended EcoRI/HindIII fragment. This plasmid product was designated pCGP672.

An XbaI/Asp718 digestion of pCGP807 (described in Example 3, above) yielded a 1.8 kb fragment containing the Hf1 cDNA, which was ligated with a 16.2 kb XbaI/Asp718 fragment from pCGP672. The plasmid thus created was designated pCGP653.

A promoter fragment of the CHS-A gene was amplified by PCR, using the oligonucleotides CHSA-782 and CHSA+34 as primers (see sequences below) and *Petunia hybrida* V30 genomic DNA as template. The PCR product was cloned into ddT-tailed pBluescript (Holton and Graham, 1991) and the orientation of the gene fragment verified by restriction enzyme mapping. The plasmid thus created was designated pCGP669. The oligonucleotide primers were designed to the published sequence of the petunia CHS-A promoter (Koes, 1988).

```
CHSA-782
        5' GTTTTCCAAATCTTGACGTG 3'

CHSA+34
        5' ACGTGACAAGTGTAAGTATC 3'
```

EXAMPLE 7

Construction of pCGP 484

Construction of pCGP484 was identical to that for pCGP485, outlined above in Example 4, except that pCGP484 contains the 3.5 kb PstI fragment (containing the chimaeric gene CHS-Hf1-PLTP) in the opposite orientation.

EXAMPLE 8

Construction of pCGP 1458

The plasmid pCGP1458 was contructed using the 10 kb binary vector pBIN19 (Bevan, 1984) as the backbone. Plasmid pBIN19 was digested with EcoRI and the resulting 5' overhang was filled in using Klenow fragment, according to standard protocols (Sambrook et al., 1989). Plasmid pCGP485 was digested with PstI to remove the chimaeric CHS/cDNA insert/PLTP gene as a 3.5 kb fragment. The 3' overhang resulting from PstI digestion was removed with T4 DNA polymerase and this fragment was then ligated into the filled in EcoRI site of the plasmid pBIN19.

EXAMPLE 9

Transformation of *E. coli* and *A. tumefaciens*

Transformation of the *Escherichza coli* strain DH5α-cells with one or other of the vectors pCGP812, pCGP90, pCGP485, pCGP628, pCGP653, pCGP484 or pCGP1458 was performed according to standard procedures (Sambrook et al., 1989) or Inoue et al., (1990).

The plasmid pCGP812, pCGP90, pCGP485, pCGP628, pCGP653, pCGP484 or pCGP1458 was introduced into the appropriate *Agrobacterium tumefaciens* strain by adding 5 µg of plasmid DNA to 100 µL of competent *Agrobacterium tumefaciens* cells prepared by inoculating a 50 mL MG/L (Garfinkel and Nester, 1980) culture and growing for 16 h with shaking at 28. The cells were then pelleted and resuspended in 0.5 mL of 85% (v/v) 100 mM $CaCl_2$/15% (v/v) glycerol. The DNA-Agrobacterium mixture was frozen by incubation in liquid $N_2$ for 2 min and then allowed to thaw by incubation at 37 for 5 min. The DNA/bacterial mixture was then placed on ice for a further 10 min. The cells were then mixed with 1 mL of MG/L media and incubated with shaking for 16 h at 28. Cells of *A. tumefaciens* carrying either pCGP812, pCGP90, pCGP485, pCGP628, pCGP653 or pCGP484 were selected on MG/L agar plates containing 100 µg/mL gentamycin. Cells of *A. tumefaciens* carrying pCGP1458 were selected on MG/L agar plates containing 100 µg/mL kanamycin. The presence of the plasmid was confirmed by Southern analysis of DNA isolated from the gentamycin-resistant transformants.

EXAMPLE 10

Transformation of Diantbus caryophyllus a. Plant Material

*Dianthus caryophyllus*, (cv. Crowley Sim, Red Sim, Laguna) cuttings were obtained from Van Wyk and Son Flower Supply, Victoria, Australia. The outer leaves were removed and the cuttings were sterilized briefly in 70% (v/v) ethanol followed by 1.25% (w/v) sodium hypochlorite (with Tween 20) for 6 minutes and rinsed three times with sterile water. All the visible leaves and axillary buds were removed under the dissecting microscope before co-cultivation.

b. Co-cultivation of Agrobacterium and Dianthus Tissue

*Agrobacterium tumefaciens* strain AGL0 (Lazo et al., 1991), containing any one of the binary vectors pCGP90, pCGP812, pCGP485 or pCGP653, was maintained at 4 on MG/L (Garfinkel and Nester, 1980) agar plates with 100 mg/L gentamycin. A single colony was grown overnight in liquid MG/L broth and diluted to $5 \times 10^8$ cells/mL next day before inoculation. Dianthus tissue was co-cultivated with Agrobacterium on Murashige and Skoog's (1962) medium (MS) supplemented with 3% sucrose (w/v), 5 mg/L α-naphthalene acetic acid (NAA), 20 µM acetosyringone and 0.8% Difco Bacto Agar (pH 5.7).

c. Recovery of Transgenic Dianthus Plants

Co-cultivated tissue was transferred to MS medium supplemented with 1 mg/L benzylaminopurine (BAP), 0.1 mg/L NAA, 150 mg/L kanamycin, 500 mg/L ticarcillin and 0.8% Difco Bacto Agar (selection medium). After three weeks, explants were transferred to fresh selection medium and care was taken at this stage to remove axillary shoots from stem explants. After 6–8 weeks on selection medium healthy adventitious shoots were transferred to hormone free MS medium containing 3% sucrose, 150 mg/L kanamycin, 500 mg/L ticarcillin, 0.8% Difco Bacto Agar. At this stage GUS histochemical assay (Jefferson, 1987) and/or NPT II dot-blot assay (McDonnell et al., 1987) was used to identify transgenic shoots. Transgenic shoots were transferred to MS medium supplemented with 3% sucrose, 500 mg/L ticarcillin and 0.4% (w/v) Gelrite Gellan Gum (Schweizerhall) for root induction. All cultures were maintained under a 16 hour photoperiod (120 µE cool white fluorescent light) at 23±2.

When plants were rooted and reached 4–6 cm tall they were acclimatised under mist. A mix containing a high ratio of perlite (75% or greater) soaked in hydroponic mix (Kandreck and Black, 1984) was used for acclimation, which typically lasts 4–5 weeks. Plants were acclimatised at 23° C. under a 14 hour photoperiod (200 µE mercury halide light).

EXAMPLE 11

Transformation of *Rosa hybrida*

1. *Rosa hybrida* cv Royalty

Plant tissues of the rose cultivar Royalty were transformed according to the method disclosed in PCT 91/04412, having publication number WO92/00371.

2. *Rosa hybrida* cv Kardinal a. Plant Material

Kardinal shoots were obtained from Van Wyk and Son Flower Supply, Victoria, Australia. Leaves were removed and the remaining shoots (5–6 cm) were sterilized in 1.25% (w/v) sodium hypochlorite (with Tween 20) for 5 minutes followed by three rinses with sterile water. Isolated shoot tips were soaked in sterile water for 1 hour and precultured for 2 days on MS medium containing 3% sucrose, 0.1 mg/L BAP, 0.1 mg/L kinetin, 0.2 mg/L Gibberellic acid, 0.5% (w/v) polyvinyl pyrrolidone and 0.25% Gelrite Gellan Gum, before co-cultivation.

b. Co-cultivation of Agrobacterium and Rosa shoot Tissue

*Agrobacterium tumefaciens* strains ICMP 8317 (Janssen and Gardner 1989) and AGL0, containing the binary vector pCGP812, was maintained at 4° C. on MG/L agar plates with 100 mg/L gentamycin. A single colony from each Agrobacterium strain was grown overnight in liquid MG/L broth. A final concentration of $5 \times 10^8$ cells/mL was prepared the next day by dilution in liquid MG/L. Before inoculation, the two Agrobacterium cultures were mixed in a ratio of 10:1 (AGL0/pCGP812:8317/pCGP812). A longitudinal cut was made through the shoot tip and an aliquot of 2 µl of the mixed Agrobacterium cultures was placed as a drop on the shoot tip.

The shoot tips were co cultivated for 5 days on the same medium used for preculture.

*Agrobacterium tumefaciens* strain AGL0, containing the binary vector pCGP1458, was maintained at 4° C. on MG/L agar plates with 100 mg/L kanamycin. A single colony from each Agrobacterium strain was grown overnight in liquid MG/L broth. A final concentration of $5 \times 10^8$ cells/mL was prepared the next day by dilution in liquid MG/L.

c. Recovery of Transgenic Rosa Plants

After co-cultivation, the shoot tips were transferred to selection medium. Shoot tips were transferred to fresh selection medium every 3–4 weeks. Galls observed on the shoot tips were excised when they reached 6–8 mm in diameter. Isolated galls were transferred to MS medium containing 3% sucrose, 25 mg/L kanamycin, 250 mg/L cefotaxime and 0.25% Gelrite Gellan Gum for shoot formation. Shoots regenerated from gall tissue were isolated and transferred to selection medium. GUS histochemical assay and callus assay were used to identify transgenic shoots. Transgenic shoots were transferred to MS medium containing 3% sucrose, 200 mg/L cefotaxime and 0.25% Gelrite Gellan Gum for root induction. All cultures were maintained under 16 hour photoperiod (60 µE cool white fluorescent light) at 23±2. When the root system was well developed and the shoot reached 5–7 cm in length the transgenic rose plants were transferred to autoclaved Debco 514110/2 potting mix in 8 cm tubes. After 2–3 weeks plants were replanted into 15 cm pots using the same potting mix and maintained at 23 under a 14 hour photoperiod (300 µE mercury halide light). After 1–2 weeks potted plants were moved to glasshouse (Day/Night temperature: 25–28/14) and grown to flowering.

EXAMPLE 12

Transformation of *Chrysanthemum morifolium* a. Plant Material

*Chrysanthemum morifolium* (cv. Blue Ridge, Pennine Chorus) cuttings were obtained from F & I Baguley Flower and Plant Growers, Victoria, Australia. Leaves were removed from the cuttings, which were then sterilized briefly in 70% (v/v) ethanol followed by 1.25% (w/v) sodium hypochlorite (with Tween 20) for 3 minutes and rinsed three times with sterile water. Internodal stem sections were used for co-cultivation.

b. Co-cultivation of Agrobacterium and Chrysanthemum Tissue

*Agrobacterium tumefaciens* strain LBA4404 (Hoekema et al., 1983), containing any one of the binary vectors pCGP90, pCGP484, pCGP485 or pCGP628, was grown on MG/L agar plates containing 50 mg/L rifampicin and 10 mg/L gentamycin. A single colony from each Agrobacterium was grown overnight in the same liquid medium. These liquid cultures were made 10% with glycerol and 1 mL aliquots transferred to the freezer (−80). A 100–200 µl aliquot of each frozen Agrobacterium was grown overnight in liquid MG/L containing 50 mg/L rifampicin and 10 mg/L gentamycin. A final concentration of $5 \times 10^8$ cells/mL was prepared the next day by dilution in liquid MS containing 3% (w/v) sucrose. Stem sections were co-cultivated, with Agrobacterium containing any one of LBA4404/pCGP90, LBA4404/pCGP484, LBA4404/pCGP485 or LBA4404/pCGP628, on co-cultivation medium for 4 days.

c. Recovery of Transgenic Chrysanthemum Plants

After co-cultivation, the stem sections were transferred to selection medium. After 3–4 weeks, regenerating explants were transferred to fresh medium. Adventitious shoots which survived the kanamycin selection were isolated and transferred to MS medium containing kanamycin and cefotaxime for shoot elongation and root induction. All cultures were maintained under a 16 hour photoperiod (80 µE cool white fluorescent light) at 23±2° C. Leaf samples were collected from plants which rooted on kanamycin and Southern blot analysis was used to identify transgenic plants. When transgenic chrysanthemum plants reached 4–5 cm in length they were transferred to autoclaved Debco 51410/2 potting mix in 8 cm tubes. After 2 weeks plants were replanted into 15 cm pots using the same potting mix and maintained at 23° C. under a 14 hour photoperiod (300 µE mercury halide light). After 2 weeks potted plants were moved to glasshouse (Day/Night temperature : 25–28° C./14° C.) and grown to flowering.

EXAMPLE 13

Southern Analysis a. Isolation of Genomic DNA from Dianthus

DNA was isolated from tissue essentially as described by Dellaporta et al., (1983). The DNA preparations were further purified by CsCl buoyant density centrifugation (Sambrook et al., 1989).

b. Isolation of Genomic DNA from Chrysanthemum

DNA was isolated from leaf tissue using an extraction buffer containing 4.5M guanidinium thiocyanate, 50 mM EDTA pH 8.0, 25 mM sodium citrate pH 7.0, 0.1M 2-mercaptoethanol, 2% (v/v) lauryl sarcosine. The plant tissue was ground to a fine powder in liquid $N_2$ following which extraction buffer was added (5 mL/g of tissue) and the solution mixed on a rotating wheel for 16 h. The mixture was then phenol: chloroform: isoamylalcohol (50:49:1) extracted twice and the genomic DNA precipitated by adding three volumes of ethanol and centrifuging for 15 min at 10,000 rpm.

c. Isolation of Genomic DNA from Rosa

DNA was extracted by grinding tissue in the presence of liquid $N_2$ in a mortar and pestle and adding 1 ml of extraction buffer (0.14M sorbitol, 0.22M Tris-HCl [pH8.0], 0.022M EDTA, 0.8M NaCl, 0.8% (w/v) CTAB, 1% N-laurylsarcosine) heated at 65° C. Chloroform (200 µl) was added and the mixture incubated at 65° C. for 15 min. Following centrifugation, the supernatant was phenol-chloroform extracted and then added to an equal volume of isopropanol, inverting to mix. This mixture was centrifuged and the pellet washed with 95% ethanol, re-centrifuged and washed with 70% ethanol. The pellet was vacuum-dried and resuspended in 30 µl TE buffer (pH 8.0).

d. Southern Blots

The genomic DNA (10 µg) was digested for 16 hours with 60 units of EcoRI and electrophoresed through a 0.7% (w/v) agarose gel in a running buffer of TAE (40 mM Tris-acetate, 50 mM EDTA). The DNA was then denatured in denaturing solution (1.5M NaCl/0.5M NaOH) for 1 to 1.5 hours, neutralized in 0.5M Tris-HCl (pH 7.5)/1.5M NaCl for 2 to 3 hours and the DNA was then transferred to a Hybond N (Amersham) filter in 20×SSC.

Southern analysis of putative transgenic Dianthus, Rosa and Chrysanthemum plants obtained after selection on kanamycin confirmed the integration of the appropriate chimaeric gene into the genome.

EXAMPLE 14

Northern Analysis a. Dianthus and Chrysanthemum RNA

Total RNA was isolated from tissue that had been frozen in liquid $N_2$ and ground to a fine powder using a mortar and pestle. An extraction buffer of 4M guanidinium isothiocyanate, 50 mM Tris-HCl (pH 8.0), 20 mM EDTA, 0.1% (v/v) Sarkosyl, was added to the tissue and the mixture was homogenized for 1 minute using a polytron at maximum speed. The suspension was filtered through Miracloth (Calbiochem) and centrifuged in a JA20 rotor for 10 minutes at 10,000 rpm. The supernatant was collected and made to 0.2 g/mL CsCl (w/v). Samples were then layered over a 10 mL cushion of 5.7M CsCl, 50 mM EDTA (pH 7.0) in 38.5 mL Quick-seal centrifuge tubes (Beckman) and centrifunged at 42,000 rpm for 12–16 hours at 23 in a Ti-70 rotor. Pellets were resuspended in TE/SDS (10 mM Tris-HCl (pH 7.5), 1 mM EDTA, 0.1% (w/v) SDS) and extracted with phenol:chloroform:isoamyl alcohol (25:24:1) saturated in 10 mM EDTA (pH 7.5). Following ethanol precipitation the RNA pellets were resuspended in TE/SDS.

RNA samples were electrophoresed through 2.2M formaldehyde/1.2% (w/v) agarose gels using running buffer containing 40 mM morpholinopropanesulphonic acid (pH 7.0), 5 mM sodium acetate, 0.1 mM EDTA (pH 8.0). The RNA was transferred to Hybond-N filters (Amersham) as described by the manufacturer and probed with $^{32}$P-labelled cDNA fragment (108 cpm/µg, $2 \times 10^6$ cpm/mL). Prehybridization (1 h at 42° C) and hybridization (16 h at 42° C) was carried out in 50% (v/v) formamide, 1M NaCl, 1% (w/v) SDS, 10% (w/v) dextran sulphate. Degraded salmon sperm DNA (100 µg/mL) was added with the $^{32}$P-labelled probe for the hybridization step.

Filters were washed in 2×SSC/1% (w/v) SDS at 65° C. for 1 to 2 hours and then 0.2 ×SSC/1% (w/v) SDS at 65° C. for 0.5 to 1 hour. Filters were exposed to Kodak XAR film with an intensifying screen at −70 for 48 hours.

Northern analysis of Dianthus cv. Red Sim transformed with plasmid pCGP90 indicated that eight of thirteen plants were positive.

b. Rosa RNA

Total RNA was extracted from petals (buds and of flowers 5 days post-harvest) according to the method of Manning, 1991.

EXAMPLE 15

$^{32}$P-Labelling of DNA Probes

DNA fragments (50 to 100 ng) were radioactively labelled with 50 μCi of [α-$^{32}$P]-dCTP using an oligolabelling kit (Bresatec). Unincorporated [α-$^{32}$P]-dCTP was removed by chromatography on a Sephadex G-50 (Fine) column.

EXAMPLE 16

Anthocyanidin Analysis

Prior to HPLC analysis the anthocyanin molecules present in petal extracts were acid hydrolysed to remove glycosyl moieties from the anthocyanidin core. The hydroxylation pattern on the B ring of the anthocyanin pigments was determined by HPLC analysis of the anthocyanidin core molecule. The HPLC system used in this analysis was a Hewlett-Packard 1050 equipped with a multiwavelength detector (MWD). Reversed phase chromatographic separations were performed on a Spherisorb S5 ODS2 cartridge column, 250 mm×4 mm ID.

a. Extraction of anthocyanins and flavonoids

Flower pigments were extracted from petal segments (ca. 50 mg) with 5 ml of methanol containing 1% (v/v) of aqueous 6M hydrochloric acid. Extracts were diluted with water (1:9) and filtered (Millex HV, 0.45μ) prior to injection into the HPLC system.

b. Hydrolysis of anthocyanins

Crude methanolic extracts (100 μL) obtained in a. above were evaporated to dryness in Pierce Reacti-Vials using a stream of dry nitrogen at room temperature. The residues were dissolved in 200 μL 2M HCl, vials were capped and then heated at 100° C. or 30 minutes. Hydrolysis mixtures were diluted with water (1:9) and filtered (Millex HV, 0.45μ) prior to HPLC analysis.

c. Chromatography

Separation of flower pigments was effected via gradient elution using the following system:

Solvent A: (triethylamine: conc. $H_3PO_4$: $H_2O$) (3:2.5:1000)

Solvent B: acetonitrile

Gradient Conditions: 5% B to 40% B over 20 minutes

Flow Rate: 1 ml/min

Temperature: 35° C.

Detection: MWD with simultaneous data acquisition at 280, 350 and 546 nm.

The anthocyanidin peaks were identified by reference to known standards. An alternative method for the analysis of anthocyanin molecules present in petal extracts is to be found in Brugliera et al., 1994.

HPLC analysis is conducted to determine the presence of delphinidin, pelargonidin and cyanidin pigments in samples of carnation, chrysanthemum and rose tissues having been transformed with one or other of the plasmids pCGP90, pCGP485, pCGP484, pCGP628, pCGP653 or pCGP1458. Representative data of pCGP90, pCGP485 and pCGP653 in transgenic carnation flowers are shown in Table 1.

TABLE 1

HPLC Analysis of pCGP90, pCGP485 and pCGP653 Transgenic Flowers

| Sample | % Delphinidin | % Pelargonidin | % Cyanidin |
|---|---|---|---|
| NON-TRANSGENIC CARNATION: | | | |
| Cultivar: Red Sim | 0 | 85.3 | 0.8 |
| TRANSGENIC CARNATION: | | | |
| Red Sim + pCGP90 | | | |
| (i) Acc #* 1933 | 1.9 | 82.7 | nd** |
| (ii) Acc # 2011 | 3.7 | 76.9 | nd |
| Red Sim + pCGP485 | | | |
| (i) Acc # 3654B | 13.0 | 75.1 | 2.3 |
| Red Sim + pCGP653 | | | |
| (i) Acc # 3660/2 | 18.1 | 71.4 | 3.2 |
| (ii) Acc # 3655 | 35.6 | 49.1 | 7.5 |

*Acc # = plant accession number
**nd = not detected

EXAMPLE 17

Preparation of Plant Extracts for Assay of 3′,5′-Hydroxylase Activity

Plant tissue was homogenised in a 10 times volume of ice-cold extraction buffer (100 mM potassium phosphate (pH 7.5), 1 mM EDTA, 0.25M sucrose, 0.25M mannitol, 0.1% (w/v) BSA, 0.1 mg/mL PMSF, 20 mM 2-mercaptoethanol and 10 mg/mL polyclar AT). The homogenate was centrifuged at 13,000 rpm in a JA20 rotor (Beckman) for 10 min at 4° C. and an aliquot of the supernatant assayed for 3′,5′-hydroxylase activity.

3′,5′-Hydroxylase Assay

3′,5′-Hydroxylase enzyme activity was measured using a modified version of the method described by Stotz and Forkmann (1982). The assay reaction mixture typically contained 195 μL of plant extract, 5 μL of 50 mM NADPH in assay buffer (100 mM potassium phosphate (pH8.0), 1 mM EDTA and 20 mM 2-mercaptoethanol), and $10^5$ dpm [$^{14}$C] naringenin in a final volume of 200 μL. Following incubation at 23 overnight, the reaction mixture was extracted twice with 0.5 mL of ethylacetate. The ethyl acetate phase was dried under vacuum and then resuspended in 10 μL of ethyl acetate. The radio-labelled flavonoid molecules were then separated on cellulose thin layer plates (Merck Art 5577, Germany) using a chloroform: acetic acid: water (10:9:1, v/v) solvent system. At the completion of the chromatography, the TLC plates were air-dried and the reaction products localised by autoradiography and identified by comparison to non-radioactive naringenin, eriodictyol, dihydroquercetin and dihydromyricetin standards which were run alongside the reaction products and visualized under UV light.

EXAMPLE 18

Transformation of various cultivars

The chimaeric genes contained in any one of the constructs pCGP90, pCGP812, pCGP628, pCGP485, pCGP653, pCGP484 or pCGP1458 is introduced into plant varieties of rose, carnation and chrysanthemum using Agrobacterium-mediated gene transfer, as described in Examples 10, 11 and 12. Integration of the appropriate chimaeric gene into the plant genome is confirmed by Southern analysis of plants obtained after kanamycin selection and HPLC analysis is used to detect the presence of anthocyanins as described in Example 16, above.

Plants successfully rendered transgenic and which are able to express the transgene in accordance with the present invention, have significant levels of 3',5'-hydroxylase enzyme activity in addition to 3',5'-hydroxylated anthocyanins (seen in Example 16), compared with non-transgenic controls which do not contain the gene necessary for the production of 3',5'-hydroxylase activity.

EXAMPLE 19

Carnation cv. Crowley Sim+pCGP 90

The plasmid pCGP90 was introduced into the carnation cultivar Crowley Sim using Agrobacterium-mediated gene transfer, as described in Example 10. Integration of the construct in the plant genome was confirmed by Southern analysis of plants obtained after kanamycin selection. Nine plants were examined for the presence of the nptII and Hf1 genes and for the production of delphinidin. Eight of the nine plants analyzed were positive for both nptII and Hf1 but HPLC analysis was unable to detect any evidence of delphinidin production by these plants (see Table 2; "Kan"=kanamycin).

TABLE 2

| # | Acc # | Kan | Hf1 | Delphinidin |
|---|-------|-----|-----|-------------|
| 1 | 1930A | + | + | − |
| 2 | 1942B | + | + | − |
| 3 | 2008B | − | − | − |
| 4 | 2217A | + | + | − |
| 5 | 2217B | + | + | − |
| 6 | 2338A | + | + | − |
| 7 | 2338B | + | + | − |
| 8 | 2338C | + | + | − |
| 9 | 2338D | + | + | − |

EXAMPLE 20

Carnation cv. Laguna+pCGP 485

The plasmid pCGP485 was introduced into the carnation cultivar Laguna using Agrobacterium-mediated gene transfer, as described in Example 10. Integration of the construct in the plant genome was confirmed by Southern analysis of plants obtained after kanamycin selection. HPLC analysis of the anthocyanin molecules present in petal extracts is carried out according to the procedure set out in Example 16, above, to show the presence of 3',5'-hydroxylated anthocyanin derivatives. These 3',5'-hydroxylated anthocyanins are only produced as a result of the expression of the exogenous DNA sequence, ie: the Hf1 cDNA sequence, introduced via transformation with the binary vector pCGP485.

EXAMPLE 21

Rose cv. Royalty+pCGP 485/pCGP 628

The plasmids pCGP485 and pCGP628 were introduced into the rose cultivar Royalty using Agrobacterium-mediated gene transfer, as referred to in Example 11. Integration of the construct in the plant genome was confirmed by Southern analysis of plants obtained after kanamycin selection. HPLC analysis of the anthocyanin molecules present in petal extracts is again carried out according to the procedure set out in Example 16, above, to show the presence of 3',5'-hydroxylated anthocyanin derivatives. These 3',5'-hydroxylated anthocyanins are only produced as a result of the expression of the exogenous DNA sequence, ie: the Hf1 cDNA sequence, introduced via transformation with either of the binary vectors pCGP485 or pCGP628.

EXAMPLE 22

Rose cv. Kardinal+pCGP 1458

The plasmid pCGP1458 was introduced into the rose cultivar Kardinal using Agrobacterium-mediated gene transfer, as described in Example 11. Integration of the construct in the plant genome was confirmed by Southern analysis of plants obtained after kanamycin selection. HPLC analysis of the anthocyanin molecules present in petal extracts is again carried out according to the procedure set out in Example 16, above, to show the presence of 3',5'-hydroxylated anthocyanin derivatives. These 3',5'-hydroxylated anthocyanins are only produced as a result of the expression of the exogenous DNA sequence, ie: the Hf1 cDNA sequence, introduced via transformation with the binary vector pCGP1458.

EXAMPLE 23

Chrysanthemum cv. BlueRidge+pCGP 484/pCGP 485/pCGP 628

The plasmids pCGP484, pCGP485 and pCGP628 were introduced into the chrysanthemum cultivar BlueRidge using Agrobacterium-mediated gene transfer, as described in Example 12. Integration of the construct in the plant genome was confirmed by Southern analysis of plants obtained after kanamycin selection. HPLC analysis of the anthocyanin molecules present in petal extracts is again carried out according to the procedure set out in Example 16, above, to show the presence of 3',5'-hydroxylated anthocyanin derivatives. These 3',5'-hydroxylated anthocyanins are only produced as a result of the expression of the exogenous DNA sequence, ie: the Hf1 cDNA sequence, introduced via transformation with any one of the binary vectors pCGP484, pCGP485 or pCGP628.

EXAMPLE 24

Altered Inflorescence

The expression of the introduced flavonoid 3',5'-hydroxylase enzyme activity in the transgenic plant is capable of having a marked effect on flower colour. Floral tissues in transgenic plants may change from the pale pinks and reds of the non-transgenic control plants to colours ranging from a darker pink/maroon to a blue/purple colour. The colours may also be described in terms of numbers from the Royal Horticultural Society's Colour Chart. In general, the changes can be described as moving the colour from the pale-to-mid pink hues of 60C/D–65C/D, to the darker bluer/purpler hues represented by many, but not all, of the colour squares between 70 and 85. It should be remembered that other biochemical and physiological conditions will affect the individual outcome and the citing of specific colours should not be interpreted as defining the possible range.

In the case of the transgenic carnation flower, Accession Number 3655, produced using the plasmid construct pCGP653 described above, an obvious bluing effect on the petals was observed. The normally-orange-red colour of Red Sim carnation cultivars (corresponding approximately to 45A/B of the Royal Horticultural Society's Colour Chart) had changed to a blue/purple hue.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

Bethesda Research Laboratories. BRL pUC host: *E. coli* DH5α™ competent cells. *Bethesda Res. Lab. Focus* 8(2): 9, 1986.

Bevan, M. *Nucleic Acids Res.* 12: 8711–8721,1984.

Brugliera, F., Holton, T. A., Stevenson, T. W., Farcy, E., Lu, C- Y. and Cornish, E. C. *Plant J.* 5(1): 81–92, 1994.

Comai, L., Moran, P. and Maslyar, D., *Plant Molecular Biology* 15: 373–381, 1990.

Dellaporta, S. J., Wood, J. and Hick, J. B. *Plant Mol. Biol. Rep.* 1: 19–21, 1983.

Ebel, J. and Hahlbrock, K. In *The Flavonoids: Advances in Research Since*1980. Harborne, J. B. (Ed.), Academic Press, New York, USA, 641–679,1988.

Forkmann, G. *Plant Breeding* 106: 1–26, 1991.

Garfinkel, D. J. and Nester, E. W. *J. Bacteriol*144: 732–743, 1980.

Hahlbrock, K. and Grisebach, H. *Annu. Rev. Plant Phystol.* 30: 105–130, 1979.

Hanahan, D. *J. Mol. Biol.* 166: 557, 1983.

Holton, T. A. PhD Thesis, University of Melbourne, Australia, 1992.

Holton, T. A. and Graham, M. W. *Nucleic Acids Res.* 19: 1156, 1991.

Horsch, R. B., Fry, J. E., Hoffmann, N. L., Eichholz, D., Rogers, S. G. and Fraley, R. T. *Science* 227: 1229–1231, 1985.

Inoue, H., Nojima, H. and Okayama, H. *Gene* 96: 23–28, 1990.

Jannsen, B- J. J. and Gardner, R. C. *Plant Mol. Biol.* 14: 61–72, 1989.

Jefferson, R. A., Kavanagh, T. A. and Bevan, M. W. *EMBO J.* 6(13): 3901–3907, 1987.

Kandreck, K. A. and Black, N. D. *Growing media for ornamental plants and turf.* p317, NSW University Press, Kensington, Australia, 1984.

Koes R. F. *Genes involved in favonoid biosynthesis in Petunia hybrida: The chalcone synthase multigene family.* PhD Thesis, Vrije Universiteit, Amsterdam, The Netherlands, 1988.

Lazo, G. R., Pascal, A. S. and Ludwig, R. A. *Bio/technology* 9: 963–967, 1991.

McDonnell, R. E., Clarke R. D., Smith, L. A. and Hinchee, M. A. *Plant Mol. Biol.Rep.* 4: 380–386, 1987

Manning, K. *Anal. Biochem.* 195: 45–50, 1991.

Sambrook, J., Fritsch, E. F. and Maniatis, T. *Molecular Cloning: A Laboratory Manual* (2nd edition). Cold Spring Harbor Laboratory Press, USA, 1989.

Schram, A. W., Jonsson, L. M. V. and Bennink, G. J. H. "Biochemistry of flavonoid synthesis in Petunia hybrida." In: Petunia Sink, K. C. (Ed.), Springer-Verlag, Berlin, Germany, pp 68–75, 1984.

Sommer, H. and Saedler, H. *Mol. Gen. Genet.* 202: 429–434, 1986.

Stafford, H. A. *Flavonoid Metabolism.* CRC Press, Inc. Boca Raton, Fla., USA, 1990.

Stotz, G. and Forkmann, G. *Z. Naturforsch* 37c: 19–23, 1982.

Vercruysse, S. A. R., Delcour, J. A. and Dondeyne, P. *J. Chromatography* 324: 495–497, 1985.

Wiering, H. and De Vlaming, P. "Inheritance and Biochemistry of Pigments." In: Petunia Sink, K. C. (Ed.), Springer-Verlag, Berlin, Germany, pp 49–65, 1984.

We claim:

1. A transgenic plant selected from rose, carnation and chrysanthemum, or progeny or flowering parts thereof wherein said transgenic plant is transformed with a genetic construct comprising a promoter from a gene encoding an enzyme of the flavonoid pathway operably linked to a gene encoding a flavonoid 3',5'-hydroxylase that hydroxylates dihydrokaempferol, and wherein said transgenic plant produces higher levels of anthocyanins derived from delphinidin relative to non-transgenic plants of the same species.

2. The transgenic plant according to claim 1 wherein the flavonoid 3',5'-hydroxylase is of petunia, verbena, delphinium, grape, iris, freesia, hydrangea, cyclamen, potato, pansy, egg plant, lisianthus or campanula origin.

3. The transgenic plant according to claim 2 wherein the flavonoid 3',5'-hydroxylase is of petunia origin.

4. The transgenic plant according to claim 2 wherein the polypeptide is a flavonoid 3',5'-hydroxylase of lisianthus origin.

5. The transgenic plant according to any one of claims 1 to 4 wherein the promoter is from the gene encoding chalcone synthase (CHS).

6. The transgenic plant according to claim 5 wherein the genetic construct is contained in a plasmid selected from pCGP484, pCGP485, pCGP653 and pCGP1458.

7. The transgenic plant according to claim 3 or claim 4 wherein said plant is a rose.

8. The transgenic plant according to claim 3 or claim 4 wherein said plant is a carnation.

9. The transgenic plant according to claim 3 or claim 4 wherein said plant is a chrysanthemum.

10. The transgenic plant according to claim 5 wherein said plant is a rose.

11. The transgenic plant according to claim 5 wherein said plant is a carnation.

12. The transgenic plant according to claim 5 wherein said plant is a chrysanthemum.

13. The transgenic plant according to claim 6 wherein said plant is a rose.

14. The transgenic plant according to claim 6 wherein said plant is a carnation.

15. The transgenic plant according to claim 6 wherein said plant is a chrysanthemum.

16. The transgenic plant according to claim 1 exhibiting altered flower color.

17. The transgenic plant according to claim 7 exhibiting altered flower color.

18. The transgenic plant according to claim 8 exhibiting altered flower color.

19. The transgenic plant according to claim 9 exhibiting altered flower color.

20. A method for producing a transgenic plant selected from rose, carnation and chrysanthemum, said method comprising introducing into said plant a gene construct comprising a promoter from a gene encoding an enzyme of the flavonoid pathway operably linked to a nucleic acid encoding a flavonoid 3'-5'-hydroxylase that hydroxylates dihydrokaempferol, wherein said transgenic plant produces higher levels of species.

21. The method according to claim 20 wherein the flavonoid 3',5'-hydroxylase is of petunia, verbena, delphinium, grape, iris, freesia, hydrangea, cyclamen, potato, pansy, egg plant, lisianthus or campanula origin.

22. The method according to claim 21 wherein the flavonoid 3',5'-hydroxylase is of petunia origin.

23. The method according to claim 21 wherein the flavonoid 3',5'-hydroxylase is of lisianthus origin.

24. The method according to any one of claims 20 to 23 wherein the promoter is from the gene encoding chalcone synthase (CHS).

25. The method according to claim 21 wherein the gene construct is contained in a plasmid selected from pGP484 having AGAL Accession No. NM 98/07526, pGP485 having AGAL Accession No. NM 98/07527, PCGP653 having AGAL Accession No. 98/07524, and pCGP1458 having AGAL Accession No. NM 98/07525.

26. The method according to claim 22 or claim 23 or claim 25 wherein said plant is a rose.

27. The method according to claim 22 or claim 23 or claim 25 wherein said plant is a carnation.

28. The method according to claim 22 or claim 23 or claim 25 wherein said plant is a chrysanthemum.

29. The method according to claim 24 wherein said plant is a rose.

30. The method according to claim 24 wherein said plant is a carnation.

31. The method according to claim 24 wherein said plant is a chrysanthemum.

32. The method according to claim 20 wherein said transgenic plant exhibits altered flower color.

33. The method according to claim 26 wherein said transgenic plant exhibits altered flower color.

34. The method according to claim 27 wherein said transgenic plant exhibits altered flower color.

35. The method according to claim 28 wherein said transgenic plant exhibits altered flower color.

36. A binary vector comprising a gene construct which integrates into a plant genome to produce the transgenic plant claim 1.

37. The binary vector according to claim 36 wherein the gene construct is a chimaeric gene construct.

38. The binary vector according to claim 37 wherein the chimaeric gene construct comprises the CHS gene promoter.

* * * * *